(12) United States Patent
Urano et al.

(10) Patent No.: US 9,610,366 B2
(45) Date of Patent: Apr. 4, 2017

(54) METHOD FOR DIAGNOSING CANCER

(71) Applicant: THE UNIVERSITY OF TOKYO, Tokyo (JP)

(72) Inventors: Yasuteru Urano, Kanagawa (JP); Tetsuo Nagano, Bunkyo-ku (JP); Masayo Sakabe, Kanagawa (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 14/163,422

(22) Filed: Jan. 24, 2014

(65) Prior Publication Data
US 2014/0206992 A1 Jul. 24, 2014

Related U.S. Application Data

(62) Division of application No. 13/521,326, filed as application No. PCT/JP2011/050299 on Jan. 12, 2011, now abandoned.

(30) Foreign Application Priority Data

Jan. 13, 2010 (JP) .................. 2010-004797

(51) Int. Cl.
| C07D 313/00 | (2006.01) |
| C07D 493/00 | (2006.01) |
| C07D 307/77 | (2006.01) |
| C07D 311/02 | (2006.01) |
| C07D 311/82 | (2006.01) |

(Continued)

(52) U.S. Cl.
CPC ...... *A61K 49/0043* (2013.01); *A61K 49/0041* (2013.01); *C07D 493/10* (2013.01)

(58) Field of Classification Search
None
See application file for complete search history.

(56) References Cited

U.S. PATENT DOCUMENTS

| 4,640,893 A | 2/1987 | Mangel et al. |
| 6,284,223 B1 | 9/2001 | Luiken |

(Continued)

FOREIGN PATENT DOCUMENTS

| EP | 2399920 | 12/2011 |
| EP | 2399920 A1 | 12/2011 |

(Continued)

OTHER PUBLICATIONS

Sakabe, M. et al. Heikan Kaikan o Keiko Seigyo Genri ni Mochiita Shinki Koso Kassei Kenshutsu Keiko Probe no Kaihatsu. Tokyo Daigaku Daigakuin Yakugakukei Kenkyuka. 2009, p. 172.*

Pompella, A. et al. Expression of γ-glutamyltransferase in cancer cells and its significance in drug resistance. Biochemical Pharmacology. 2006, vol. 71, p. 233.*

Urano, Y. et al. Selective molecular imaging of viable cancer cells with pH-activatable fluorescence probes. Nature Medicine—Technical Reports. 2009, vol. 15, p. 108.*

Yasuteru Urano et al., "Selective molecular imaging of viable cancer cells with pH-activatable fluorescence probes", Nature Medicine, vol. 15, No. 1, Jan. 2009, pp. 104-109.

(Continued)

*Primary Examiner* — Nobel Jarrell
*Assistant Examiner* — Ben S Michelson
(74) *Attorney, Agent, or Firm* — Greenblum & Bernstein, P.L.C.

(57) ABSTRACT

Methods for identifying the presence of cancerous cells or tissue by: applying a compound of formula (I), or salts thereof, to a living body,

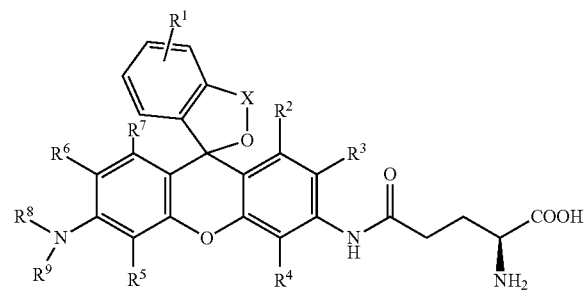

wherein $R^1$ represents hydrogen or the same or different one to four substituents; $R^2$, $R^3$, $R^4$, $R^5$, $R^6$, and $R^7$ independently represent hydrogen, hydroxy, alkyl, or halogen; $R^8$ and $R^9$ independently represent hydrogen or alkyl; and X represents $C_1$-$C_3$ alkylene; and detecting fluorescence emitted by a compound of formula (II),

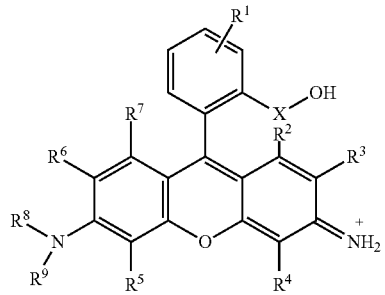

wherein $R^1$, $R^2$, $R^3$, $R^4$, $R^5$, $R^6$, $R^7$, $R^8$, and $R^9$ are as defined above; wherein fluorescence emitted by a compound of formula (II) is indicative of the presence of cancerous cells or tissue.

20 Claims, 4 Drawing Sheets

(51) Int. Cl.

| | | |
|---|---|---|
| *A61B 6/00* | (2006.01) | |
| *A61B 17/24* | (2006.01) | |
| *A61B 17/26* | (2006.01) | |
| *A61B 5/00* | (2006.01) | |
| *A61B 8/00* | (2006.01) | |
| *A61B 10/00* | (2006.01) | |
| *A61K 31/35* | (2006.01) | |
| *A61K 49/00* | (2006.01) | |
| *C07D 493/10* | (2006.01) | |

(56) References Cited

U.S. PATENT DOCUMENTS

| | | |
|---|---|---|
| 6,299,860 B1 | 10/2001 | Luiken |
| 6,652,836 B2 | 11/2003 | Luiken |
| 6,797,521 B2 | 9/2004 | Grissom et al. |
| 6,905,884 B2 | 6/2005 | Grissom et al. |
| 2001/0055566 A1 | 12/2001 | Luiken |
| 2004/0082863 A1 | 4/2004 | McGreevy et al. |
| 2012/0052518 A1 | 3/2012 | Nagano et al. |

FOREIGN PATENT DOCUMENTS

| | | |
|---|---|---|
| JP | 2004-527299 | 9/2004 |
| JP | 2004-535371 | 11/2004 |
| JP | 5588962 B2 | 9/2014 |
| WO | 02/074171 | 9/2002 |
| WO | 02/080778 | 10/2002 |
| WO | 03/099780 | 12/2003 |
| WO | 2010/095450 | 8/2010 |

OTHER PUBLICATIONS

Masayo Sakabe, "Heikan Kaikan 0 Keiko Seigyo Genri ni Mochiita Shinki Koso Kassei Kenshutsu Keiko Probe no Kaihatsu", Heisei 21 Nen 3 Gatsu Shushi Katei Shuryo Yoteisha Shushi Ronbun Happyo Yoshishu (Heisei 21 Nen 3 Gatsu 2, 3, 4, 5, Nichi), Tokyo Daigaku Daigakuin Yakugakukei Kenkyuka, Mar. 2009, pp. 171-172.

A. Pompella et al., "Expression of γ-glutamyltransferase in cancer cells and its significance in drug resistance", Biochemical Pharmacology, vol. 71, 2006, pp. 231-238.

Search report from International Application No. PCT/JP2011/050299, mail date is Mar. 8, 2011.

International Preliminary Report on Patentability and Written Opinion for International Application No. PCT/JP2011/050299, mail date is Aug. 16, 2012.

Hisataka Kobayashi et al., "Fluorescence-guided real-time endoscopic peritoneal ovarian cancer detection using a gamma-glutamyltransferase sensitive ultra-fast enzyme-activatable imaging probe", World Molecular Imaging Congress 2010, XP055062747, Sep. 9, 2010.

Search report from E.P.O., mail date is May 24, 2013.

European Office Action issued with respect to application No. 11732870.8, mail date is Jan. 26, 2015.

Japanese Office Action issue with respect to application No. 2011-559976, mail date Dec. 10, 2014.

European Office Action in respect European Application No. 11 732 870.8, dated Nov. 12, 2015.

European Office Action in respect to European Application No. 11 732 870.8, dated Aug. 10, 2016.

* cited by examiner

METHOD FOR DIAGNOSING CANCER

CROSS-REFERENCE TO RELATED APPLICATIONS

The present application is a divisional of U.S. application Ser. No. 13/521,326 which is a National Stage of International Patent Application No. PCT/JP2011/050299 filed Jan. 12, 2011, which claims priority to Japanese Application No. 2010-004797 filed Jan. 13, 2010. The disclosures of U.S. application Ser. No. 13/521,326 and International Patent Application No. PCT/JP2011/052841 are incorporated by reference herein in their entireties.

TECHNICAL FIELD

The present invention relates to an agent for diagnosing cancer. More specifically, the present invention relates to an agent for diagnosing cancer that specifically emits fluorescence in a cancerous tissue within a short time when applied to a part in which presence of a cancerous tissue is suspected.

BACKGROUND ART

Imaging diagnosis techniques such as those based on PET or MRI have been widely used as methods for diagnosing cancers in recent years. However, by means of these techniques, it is difficult to find microcarcinomas not larger than 1 cm.

Moreover, these techniques also have problems that very large scale instruments are required for imaging, and they are not suitable as diagnostic methods for identifying a cancerous lesion to be excised by a surgeon during surgery, endoscopy, or the like.

A cancer imaging method utilizing a probe complex consisting of a combination of an antibody against a cancer and a pH-sensitive fluorescent probe has recently been reported (Nat. Med., 15, pp. 104-109, 2009). This method has a characteristic feature in that specific imaging of a cancerous tissue with fluorescence is achievable.

However, this method has problems that sensitivity of the probe complex used in this method is insufficient, and that a time of 1 hour or longer is required before a cancerous lesion becomes detectable after the administration of the probe. From these reasons, the method has not yet been practically used as a method for prompt diagnosis of a cancerous tissue during surgery or the like.

As fluorescent probes utilizing a xanthene structure, fluorescent probes for measurement of protease having superior quick responsiveness and quantifiability have been developed, and as a fluorescent probe that specifically reacts with γ-glutamyltransferase (GGT) to give intense fluorescence within a short time, γ-Glu-RhoHM has also been reported (Masayo Sakabe, "Development of novel fluorescent probes for enzyme activity detection utilizing ring opening for the basis of fluorescence control", Master's thesis in Graduate School of Pharmaceutical Sciences, The University of Tokyo, presented in the Master's thesis presentation meeting on Mar. 5, 2009, Abstract is readable in The Library of Faculty of Pharmaceutical Sciences, The University of Tokyo). However, use of this fluorescent probe for cancer diagnosis has not yet been reported.

In addition, it has been reported that promotion of expression of γ-glutamyltransferase is observed in cancer cells, and this expression promotion relates to drug resistance (Biochemical Pharmacology, 71, pp. 231-238, 2006). However, any diagnostic method for identifying a cancer cell or a cancerous tissue with high accuracy by detecting γ-glutamyltransferase has not been reported so far.

PRIOR ART REFERENCES

Non-Patent Documents

Non-patent document 1: Biochemical Pharmacology, 71, pp. 231-238, 2006
Non-patent document 2: Nat. Med., 15, pp. 104-109, 2009
Non-patent document 3: Masayo Sakabe, Master's thesis in Graduate School of Pharmaceutical Sciences, The University of Tokyo, presentation in the Master's thesis presentation meeting on Mar. 5, 2009, and Abstracts of Master's theses readable in The Library of Faculty of Pharmaceutical Sciences, The University of Tokyo

SUMMARY OF THE INVENTION

Object to be Achieved by the Invention

An object of the present invention is to provide an agent for diagnosing cancer.

More specifically, the object of the present invention is to provide an agent for diagnosing cancer that specifically emits fluorescence in a cancerous tissue when applied to a part in which presence of a cancerous tissue is suspected, and also to provide an agent for diagnosing cancer that can achieve prompt identification of a cancerous tissue in a surgical operation, endoscopy, or the like.

Means for Achieving the Object

The inventors of the present invention conducted various researches to achieve the aforementioned object. As a result, they found that when a compound represented by the following general formula (I), which acts as a fluorescent probe for measurement of γ-glutamyltransferase, was applied to a part in which presence of a cancerous tissue is suspected, intense fluorescence was specifically emitted only from the cancerous tissue, and intensity of the fluorescence reached to a sufficient level within a shot time, e.g. approximately within several tens of seconds to several minutes, to successfully achieve extremely easy identification of the cancerous tissue. The present invention was accomplished on the basis of the aforementioned findings.

The present invention thus provides an agent for diagnosing cancer comprising a compound represented by the following general formula (I):

[Formula 1]

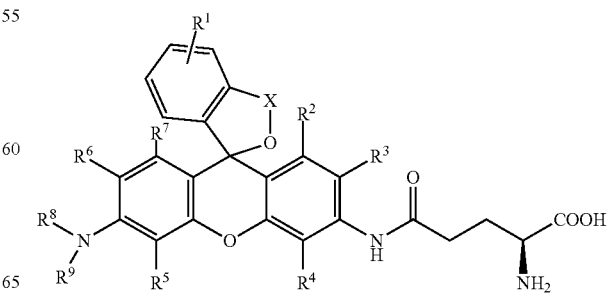

wherein R¹ represents hydrogen atom, or the same or different one to four substituents binding to the benzene ring; R², R³, R⁴, R⁵, R⁶, and R⁷ independently represent hydrogen atom, hydroxyl group, an alkyl group, or a halogen atom; R⁸ and R⁹ independently represent hydrogen atom, or an alkyl group; and X represents a C₁-C₃ alkylene group, or a salt thereof as an active ingredient.

According a preferred embodiment of the aforementioned invention, there is provided the aforementioned agent for diagnosing cancer comprising the aforementioned compound or a salt thereof, wherein R¹, R², R³, R⁴, R⁵, R⁶, R⁷, R⁸, and R⁹ are hydrogen atoms, and X is methylene group.

According to other preferred embodiments of the present invention, there are provided the aforementioned agent for diagnosing cancer, which is used for a surgical treatment of a cancer or a diagnosis for a cancer; the aforementioned agent for diagnosing cancer, wherein the surgical treatment of a cancer or the diagnosis for a cancer is an open surgery such as craniotomy, thoracotomy or laparotomy, an endoscopic surgery, or endoscopy; and the aforementioned agent for diagnosing cancer, which is used for quick diagnosis during surgery.

The present invention also provides use of a compound represented by the aforementioned general formula (I) or a salt thereof for manufacture of the aforementioned agent for diagnosing cancer.

From another aspect of the present invention, there is provided a method for diagnosing a cancer, which comprises the following steps:
(1) the step of applying a compound represented by the aforementioned general formula (I) or a salt thereof to a part of a living body containing a cancerous tissue, and
(2) the step of identifying the cancerous tissue in the part of a living body by detecting fluorescence emitted by a compound represented by the following general formula (II):

[Formula 2]

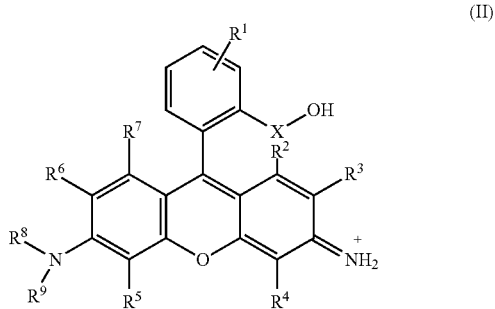

(II)

wherein R¹, R², R³, R⁴, R⁵, R⁶, R⁷, R⁸, R⁹, and X have the same meanings as those defined above) or a salt thereof which is generated in the cancerous tissue.

Effect of The Invention

By using the agent for diagnosing cancer provided by the present invention, intense fluorescence is specifically emitted only from a cancerous tissue, and accordingly, it becomes possible to accurately identify a cancerous tissue. Further, the agent for diagnosing cancer of the present invention gives extremely intense fluorescence in a cancerous tissue within a short time of from about several tens of seconds to several minutes, the agent has a characteristic feature in that extremely quick identification of a cancerous tissue during a surgical operation or a diagnosis is achieved. Furthermore, the agent also has a characteristic feature in that diagnosis using the agent for diagnosing cancer of the present invention can be carried out by means of a visible light which is safe for living bodies.

MODES FOR CARRYING OUT THE INVENTION

Figure 1:
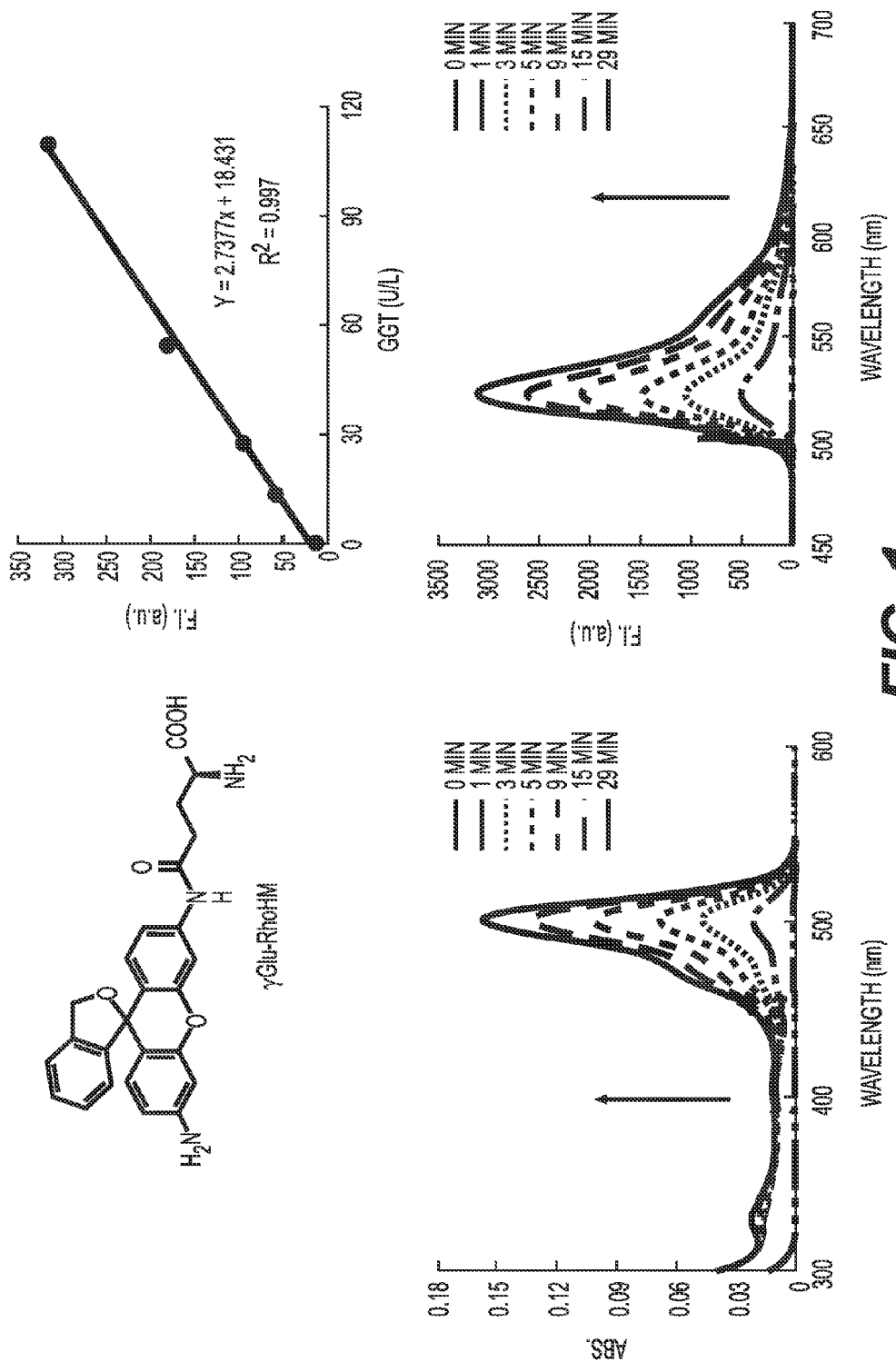
FIG. 1 This figure shows changes of absorption and fluorescence spectrum of Compound (2) (γGlu-RhoHM) after the reaction with γ-glutamyltranspeptidase (GGT), and the reaction quantifiability of γGlu-RhoHM.

The alkyl group mentioned in this specification may be a linear, branched or cyclic alkyl group, or may be an alkyl group consisting of a combination thereof. Although the carbon number of the alkyl group is not particularly limited, the number may be, for example, about 1 to 6, preferably about 1 to 4. The alkyl group mentioned in this specification may have one or more arbitrary substituents. Examples of the substituent include, for example, an alkoxyl group, a halogen atom (the halogen atom may be any of fluorine atom, chlorine atom, bromine atom, and iodine atom), amino group, a mono- or di-substituted amino group, a substituted silyl group, an acyl group, and the like, but the substituent is not limited to these examples. When the alkyl group has two or more substituents, they may be the same or different. The above descriptions are similarly applied to alkyl moieties of other substituents containing an alkyl moiety (for example, an alkyloxy group, an aralkyl group, and the like).

The aryl group mentioned in this specification may be either a monocycle aryl group or a condensed polycyclic aryl group, and may contain one or more heteroatoms (for example, oxygen atom, nitrogen atom, sulfur atom and the like) as ring-constituting atoms. The aryl group mentioned in this specification may have one or more arbitrary substituents on the ring. Examples of the substituent include, for example, an alkoxyl group, a halogen atom, amino group, a mono- or di-substituted amino group, a substituted silyl group, an acyl group, and the like, but the substituent is not limited to these examples. When the aryl group has two or more substituents, they may be the same or different. The above descriptions are similarly applied to aryl moieties of other substituents containing an aryl moiety (for example, an aryloxy group, an aralkyl group, and the like).

R¹ represents hydrogen atom, or one to four substituents binding to the benzene ring. Examples of the substituent include, for example, an alkyl group, an alkoxyl group, a halogen atom, amino group, a mono- or di-substituted amino group, a substituted silyl group, an acyl group, and the like, but the substituent is not limited to these examples. When there are two or more substituents on the benzene ring, they may be the same or different. As $R^1$, hydrogen atom is preferred.

$R^2$, $R^3$, $R^4$, $R^5$, $R^6$ and $R^7$ independently represent hydrogen atom, hydroxyl group, an alkyl group, or a halogen atom. It is preferred that $R^2$ and $R^7$ are hydrogen atoms. It is also preferred that $R^3$, $R^4$, $R^5$ and $R^6$ are hydrogen atoms. It is more preferred that all of $R^2$, $R^3$, $R^4$, $R^5$, $R^6$ and $R^7$ are hydrogen atoms.

$R^8$ and $R^9$ independently represent hydrogen atom or an alkyl group. When both $R^8$ and $R^9$ represent an alkyl group, they may be the same or different. For example, it is preferred that both $R^8$ and $R^9$ are hydrogen atoms, or $R^8$ is an alkyl group and $R^9$ is hydrogen atom, and it is more preferred that both $R^8$ and $R^9$ are hydrogen atoms.

X represents a $C_1$-$C_3$ alkylene group. The alkylene groups may be either a linear alkylene group or a branched alkylene group. For example, in addition to methylene group (—$CH_2$—), ethylene group (—$CH_2$—$CH_2$—), and propylene group (—$CH_2$—$CH_2$—$CH_2$—), —$CH(CH_3)$—, —$CH_2$—$CH(CH_3)$—, —$CH(CH_2CH_3)$—, and the like can also be used as branched alkylene groups. Among them, methylene group and ethylene group are preferred, and methylene group is more preferred.

The compound represented by the aforementioned general formula (I) may exist as a salt. Examples of the salt include a base addition salt, an acid addition salt, an amino acid salt, and the like. Examples of the base addition salt include, for example, metal salts such as sodium salts, potassium salts, calcium salts, and magnesium salts; ammonium salts, and organic amine salts such as triethylamine salts, piperidine salts, and morpholine salts. Examples of the acid addition salt include, for example, mineral acid salts such as hydrochlorides, sulfates, and nitrates, and organic acid salts such as methanesulfonates, p-toluenesulfonates, citrates, and oxalates. Examples of the amino acid salt include glycine salts and the like. However, salts of the compounds of the present invention are not limited to these examples.

The compound represented by the general formula (I) may have one or two or more asymmetric carbons depending on the type of the substituent, and stereoisomers such as optical isomers or diastereoisomers may exist. Such stereoisomers in pure forms, arbitrary mixtures of stereoisomers, racemates and the like all fall within the scope of the present invention.

The compound represented by the general formula (I) or a salt thereof may exist as a hydrate or a solvate, and any of these substances fall within the scope of the present invention. The type of solvent that forms the solvate is not particularly limited. For example, such solvents as ethanol, acetone and isopropanol can be exemplified.

The compound of represented by the general formula (I) can be readily prepared from, for example, a xanthene compound having amino groups at the 3- and 6-positions and 2-carboxyphenyl group or a 2-alkoxycarbonylphenyl group at the 9-position or the like used as the starting material by, for example, converting the 2-carboxyphenyl group or 2-alkoxycarbonylphenyl group at the 9-position into a hydroxyalkyl group and then acylating the amino group at the 3-position. As the 3,6-diaminoxanthene compound usable as the starting material, examples include, for example, rhodamine 110, rhodamine 123 and the like, which are all commercially available, but the 3,6-diaminoxanthene compound is not limited to these examples, and an appropriate xanthene compound can be chosen depending on the structure of the objective compound.

A preparation method for a typical compound among the compounds of the present invention represented by the general formula (I) is specifically described in the examples mentioned in this specification, and accordingly, those skilled in the art can readily prepare an arbitrary compound among the compounds represented by the general formula (I), by referring to the disclosures of the present specification, and appropriately choosing starting materials, reagents, reaction conditions, and the like, as required.

The compound represented by the general formula (I) per se is substantially non-fluorescent. Whilst, when the γ-glutamyl group is hydrolyzed by γ-glutamyltransferase, the compound promptly becomes a tautomer having an open ring structure to give a strongly fluorescent compound represented by the general formula (II). Therefore, the agent for diagnosing cancer of the present invention comprising the compound represented by the general formula (I) or a salt thereof as an active ingredient has a property that the agent is hydrolyzed by γ-glutamyltransferase specifically and strongly expressed in a cancerous tissue to give a compound represented by general formula (II) that emits intense fluorescence in the cancerous tissue, and by applying the agent to a part in which presence of a cancerous tissue is suspected, only a cancerous tissue comes to specifically emit intense fluorescence within several tens of seconds to several minutes.

For example, when the compound represented by the general formula (I) or a salt thereof is irradiated with an excitation light of about 440 to 500 nm in a neutral pH region, the compound emits almost no fluorescence, whilst the compound represented by the general formula (II) has a property of emitting strong fluorescence under the same conditions (for example, emission: 524 nm). Therefore, when diagnosis is carried out by using the agent for diagnosing cancer of the present invention, usually a visible light of about 440 to 500 nm, preferably a visible light of about 445 to 490 nm, more preferably a visible light of about 450 to 480 nm, can be irradiated. The wavelength of fluorescence to be observed is usually about 510 to 800 nm, and for example, it is preferable to observe fluorescence of about 516 to 556 nm.

In this specification, the term "cancerous tissue" means an arbitrary tissue containing a cancer cell. The term "tissue" should be construed in its broadest sense, including a part and whole of organs, and it should not be construed in any limitative way. The agent for diagnosing cancer of the present invention has an action of detecting γ-glutamyltransferase specifically and strongly expressed in a cancerous tissue, and accordingly, the cancerous tissue is preferably a tissue highly expressing γ-glutamyltransferase. Such cancerous tissue is explained in, for example, Biochemical Pharmacology, 71, pp. 231-238, 2006. Further, in this specification, the term "diagnosis" should be construed in its broadest sense, including macroscopically or microscopically confirming presence of a cancerous tissue in an arbitrary part of a living body.

The agent for diagnosing cancer of the present invention can be used, for example, during a surgical operation or a diagnosis. In this specification, the term "surgical operation" encompasses arbitrary surgeries applied for cancer therapy including open surgeries such as craniotomy, thoracotomy and laparotomy, skin operations, and the like, which are accompanied by incision, as well as endoscopic surgeries using gastroscope, large intestine endoscope, laparoscope, thoracoscope, or the like. The term "diagnosis" encompasses diagnostic treatments using an endoscope such as gastroscope and large intestine endoscope, procedures accompanying diagnostic treatments such as excision and collection of tissues, as well as diagnostic treatments performed for tissues extracted and collected from living bodies, and the like. These terms should be construed in their broadest senses, and they should not be construed in any limitative way.

Cancers that can be diagnosed with the agent for diagnosing cancer of the present invention are not particularly limited, and encompass arbitrary malignant tumors including sarcoma. The agent is preferably used for diagnosis of a solid carcinoma. As one of preferred embodiments, for example, the agent for diagnosing cancer of the present invention can be applied to a part or whole of a field of surgical operation performed macroscopically or under an endoscope by an appropriate method such as spray, application, or infusion, and after several tens of seconds to several minutes, the part applied can be irradiated with a light of a wavelength of about 500 nm. When a cancerous tissue is included in the part applied, the tissue comes to emit fluorescence, and therefore the tissue is identified as a cancerous tissue, and is excised together with surrounding tissues. For example, in surgical treatments of typical carcinomas such as gastric cancer, lung cancer, breast cancer, colon cancer, liver cancer, gall bladder cancer, and pancreatic cancer, definite diagnosis can be performed for carcinoma tissues that can be macroscopically confirmed, and infiltration, metastasis and the like into lymphoid tissues such as lymph nodes, as well as circumferential organs and tissues can also be diagnosed. Therefore, it becomes possible to perform quick diagnosis during a surgery to determine a region to be excised.

As another preferred embodiment, for example, in gastroscopy or large intestine endoscopy, the agent for diagnosing cancer of the present invention can be applied to a part to be tested by an appropriate method such as spray, application, or infusion, and after several tens of seconds to several minutes, the part applied can be irradiated with a light of a wavelength of about 500 nm, and when a tissue emitting fluorescence is detected, the tissue can be identified as a cancerous tissue. When a cancerous tissue is identified in endoscopy, diagnostic or therapeutic resection can be performed against the tissue.

A concentration for application of the agent for diagnosing cancer of the present invention is not particularly limited. The agent can be preferably applied to a tissue, in which presence of a cancerous tissue is suspected, as a solution of a concentration of about 1 to 1,000 μM, and the agent is generally preferably applied under a neutral condition. The agent can be used in the range of, for example, pH 5.0 to 9.0, preferably pH 6.0 to 8.0, more preferably pH 6.8 to 7.6. Although the compound represented by the aforementioned general formula (I) or a salt thereof, per se, may be used as the agent for diagnosing cancer of the present invention, the compound or a salt thereof may be used as a composition by mixing the compound or a salt thereof with additives generally used for preparation of reagents, if necessary. For example, as additives for use of reagents under a physiological condition, such additives as dissolving aids, pH adjusters, buffers, and isotonic agents can be used, and amounts of these additives can suitably be chosen by those skilled in the art. Such a composition may be provided as those in appropriate forms, for example, powdery mixtures, lyophilized products, granules, tablets, solutions and the like, and they can be dissolved in water for injection or an appropriate buffer at the time of use, and applied.

EXAMPLES

The present invention will be more specifically explained with reference to examples. However, the scope of the present invention is not limited to the following examples.

Example 1

Compound (2) was prepared according to the following scheme.

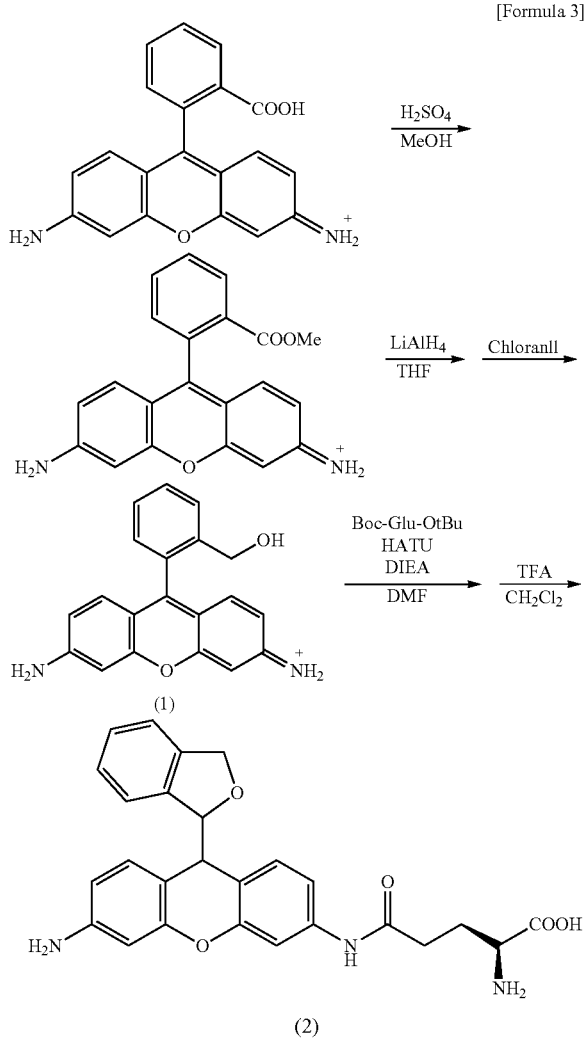

[Formula 3]

(a) Synthesis of Compound (1) (RhoHM)

Rhodamine 110 (285 mg, 0.8 mmol, 1 eq.) was dissolved in methanol (10 mL), the solution was added with sulfuric acid, and the mixture was stirred at 80° C. for 10 hours under an argon atmosphere. The reaction solvent was removed under reduced pressure, and the residue was washed with saturated aqueous sodium hydrogencarbonate and water. The resulting solid was dissolved in tetrahydrofuran (THF, 10 mL), the solution was added with a 5 M sodium methoxide solution (in methanol, 400 μL, 0.8 mmol, 1 eq.) at 0° C. under an argon atmosphere, and the mixture was stirred for 10 minutes. Then, the mixture was added with lithium aluminum hydride (333 mg, 8 mmol, 10 eq.), and the mixture was stirred for 3 hours. The reaction mixture was added with saturated aqueous ammonium chloride (5 mL), the solvent was removed under reduced pressure, and the resulting solid was extracted with dichloromethane and a saturated aqueous solution of tartaric acid tetrahydrate potassium and sodium salt. The organic layer was added with sodium sulfate, and filtered, and then the solvent was removed to obtain a solid. The resulting solid was dissolved in dichloromethane, the solution was added with chloranil (196 mg, 1 mmol, 1 eq.), and the mixture was stirred at room temperature for 30 minutes. The solvent was removed under reduced pressure, and the residue was purified by silica gel chromatography (dichloromethane/methanol=10:1) to obtain the objective compound (104 mg, 41%).

$^1$H NMR (300 MHz, CD$_3$OD): δ 7.64 (d, 1H, J=7.7 Hz), 7.56 (t, 1H, J=7.6 Hz), 7.44 (t, 1H, J=7.5 Hz), 7.17 (d, 1H, J=7.5 Hz), 7.03-7.00 (m, 2H), 6.71-6.74 (m, 4H), 4.23 (s, 2H)

$^{13}$C NMR (400 MHz, CD$_3$OD): δ 161.5, 159.9, 159.6, 141.0, 133.4, 132.2, 131.3, 130.3, 129.5, 128.8, 118.0, 115.0, 98.4, 62.8

HRMS (ESI+) Calcd for [M+H]$^+$, 317.12900. Found, 317.12862 (−0.38 mmu)

(b) Synthesis of Compound (2) (γGlu-RhoHM)

Compound (1) (0.05 mmol, 1 eq.), HATU (0.11 mmol, 2 eq.) and N,N-diisopropylethylamine (0.11 mmol, 2 eq.) were dissolved in dimethylformamide (DMF, 2 mL), and the solution was stirred at 0° C. for 10 minutes under an argon atmosphere. Then, DMF (0.5 mL) dissolving Boc-Glu-OtBu (0.05 mmol, 1 eq.) was added to the solution, and the mixture was stirred for 15 hours. The reaction solvent was removed under reduced pressure, then the obtained solid was dissolved in dichloromethane (2 mL) and trifluoroacetic acid (TFA, 2 mL), and the solution was stirred for 30 minutes. The solvent was removed, and the residue was purified by using HPLC (Eluent A: H$_2$O containing 0.1% TFA, Eluent B: CH$_3$CN (80%) and H$_2$O (20%) containing 0.1% TFA, A/B=80/20 to 0/100 over 40 minutes) to obtain the objective compound.

Compound (2)

$^1$H NMR (400 MHz, CD$_3$OD): δ 8.39 (s, 1H), 7.62-7.61 (m, 2H), 7.50-7.47 (m, 1H), 7.39 (d, 1H, J=7.8 Hz), 7.24-7.22 (m, 3H), 6.94 (d, 1H, J=8.3 Hz), 6.86 (s, 1H), 4.25 (s, 2H), 3.96 (t, 1H, J=6.3 Hz), 2.71-2.69 (m, 2H), 2.30-2.27 (m, 2H)

$^{13}$C NMR (400 MHz, CD$_3$OD): δ173.4, 171.8, 164.5, 163.1, 160.7, 157.1, 148.7, 141.2, 134.9, 131.9, 131.7, 130.5, 129.8, 129.0, 121.4, 119.4, 118.5, 106.9, 98.5, 63.1, 53.5, 33.4, 26.6

HRMS (ESI+) Calcd for [M+H]$^+$, 446.17160. Found, 446.17195 (+0.36 mmu).

Example 2

Compound (2) (γGlu-RhoHM) formed by binding the acyl residue derived from glutamic acid to one amino group of Compound (1) (RhoHM) was dissolved in a neutral phosphate buffer, and γ-glutamyltranspeptidase (GGT, equine kidney, SIGMA G9270-100UN) was reacted with the solution. Specifically, 3 μL of a 5 μM solution of the compound in dimethyl sulfoxide (DMSO) was dissolved at a final concentration of 5 μM in 3 mL of a 0.1 M sodium phosphate buffer (pH 7.4), and GGT (1.1 U) was added for the enzymatic reaction at 37° C. The excitation wavelength was 501 nm. As a result, a compound having an open ring structure was produced by hydrolysis of the acyl group, and remarkable elevations of absorption and fluorescence intensity were immediately observed (FIG. 1).

The DMSO solution of the compound (5 mM) in a volume of 3 μL was dissolved in 3 mL of a 0.1 M sodium phosphate buffer (pH 7.4) at a final concentration of 5 μM, and the enzymatic reaction was performed at 37° C. The values of fluorescence intensity observed with each amount of the enzyme 9 minutes after the addition of the enzyme were plotted. The excitation wavelength was 501 nm, and the fluorescence emission wavelength was 524 nm. As a result, the compound gave linear increase of fluorescence intensity in an added GGT amount-dependent manner (FIG. 1).

Example 3

Enzyme specificity of Compound (2) was examined. The DMSO solution (5 mM) in a volume of 3 μL was dissolved in 3 mL of a 0.1 M sodium phosphate buffer (pH 7.4) at a final concentration of 5 μM, and LAP (0.4 U) was added to the solution to perform the enzymatic reaction at 37° C. As a result, increase of fluorescence intensity was not observed after the reaction of Compound (2) (γGlu-RhoHM) with LAP. Whilst, Compound (2) reacted with GGT to give remarkable fluorescence intensity (Example 2), and therefore it was considered that γGlu-RhoHM specifically detected GGT.

Example 4

Fluorescence Imaging Using Cancer Model Mouse

Disseminated metastasis of ovarian cancer to the peritoneum is known as a generally-occurring lethal complication of ovarian cancer. Such metastasis to the peritoneum begins to occur at a relatively early stage of ovarian cancer, the tumor invades the chorionic membrane, and falls into the abdominal cavity, and as a result, the tumor metastasizes to the other organs in the abdominal cavity as seeds are scattered (dissemination metastasis). In order to experimentally reproduce this phenomenon, SHIN3 cells of ovarian cancer origin were intraperitoneally administered to athymic mice to prepare a peritoneal dissemination model (Neoplasia, 8, pp. 607-612, 2006).

The SHIN3 cells derived from human ovarian cancer were cultured at 37° C. in the RPMI 1640 medium containing 10% FBS, 100 U/mL of penicillin, and 100 μg/mL of streptomycin under 5% CO$_2$. After the cells reached subconfluent, the cells were washed with PBS (phosphate buffered saline), and removed with Trypsin-EDTA so that individual cells were separated. The treated cells were centrifuged (100×g, 4° C., 3 minutes), and after the supernatant was discarded, ice-cooled PBS was added to the cells to suspend them at a cell density of 1×10$^6$ cells/300 μL. The prepared cell suspension was immediately intraperitoneally administered to about 8-week old athymic mice in a volume of 300 μL (1×10$^6$ cells) per mouse. The treated mice were bred for about 5 to 10 days. Formation of a large number of tumors of about 0.1 mm to several millimeters on sites adjacent to the pancreas and spleen and on the mesenterium was confirmed generally in this period.

A solution of Compound (2) (γGlu-RhoHM) in PBS (50 μM) in a volume of 300 μL was intraperitoneally (i.p.) administered to the peritoneal dissemination model mice. Fluorescence imaging was performed by irradiating an excitation light of 450 to 480 nm from the outside of the mouse body under anesthesia 30 minutes after the i.p. administration, and observing fluorescence of 516 to 556 nm. Further, after the mice were sacrificed with $CO_2$ gas, and exsanguination was performed, abdominal section was performed with surgery appliances for small animals to expose the abdominal cavity, an excitation light of 445 to 490 nm was irradiated, and fluorescence was measured at every 10 nm from 520 to 800 nm to obtain fluorescence spectrum images.

Figure 2:
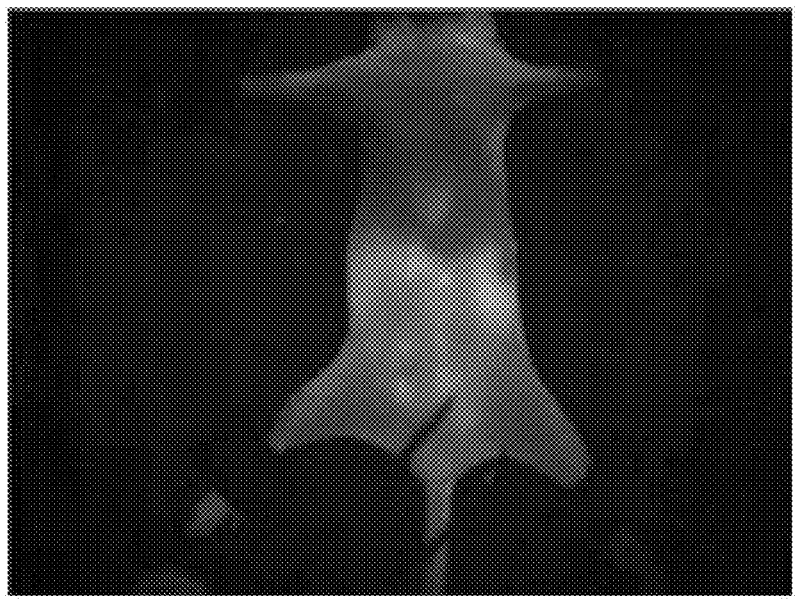
FIG. 2 This figure shows an image obtained by imaging using Compound (2) from the outside of the body.
Figure 3:
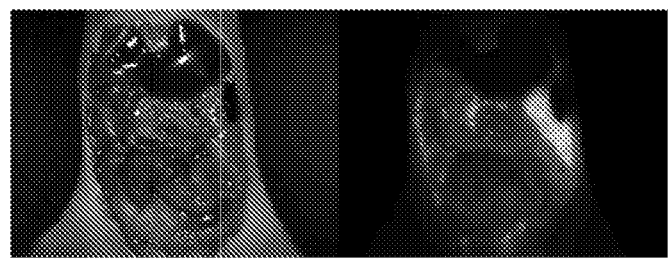
FIG. 3 This figure shows an intraabdominal image after laparotomy (upside) and mesenteric image after laparotomy (downside) obtained by imaging using Compound (2). In each image, a white light image is shown on the left side, and a fluorescence image is shown on the right side.
Figure 3:
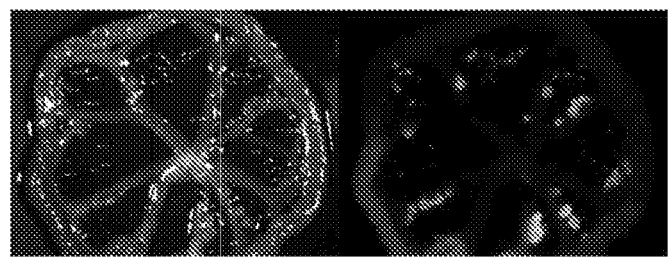

As a result, strong green fluorescence was observed in a cancer site-specific manner. An image obtained by the imaging performed from the outside of bodies before the abdominal section are shown in FIG. 2 (30 minutes after the administration of Compound (2)). In FIG. 3, the upper image is obtained by intraperitoneal imaging performed after the abdominal section (30 minutes after the administration of Compound (2)), and the lower image is obtained by mesentery imaging performed after the abdominal section (30 minutes after the administration of Compound (2)). In each image, a white light image is shown on the left side, and a fluorescence image is shown on the right side.

Example 5

Live Imaging of Cancer Model Mouse Using Fluorescent Endoscope

Figure 4:
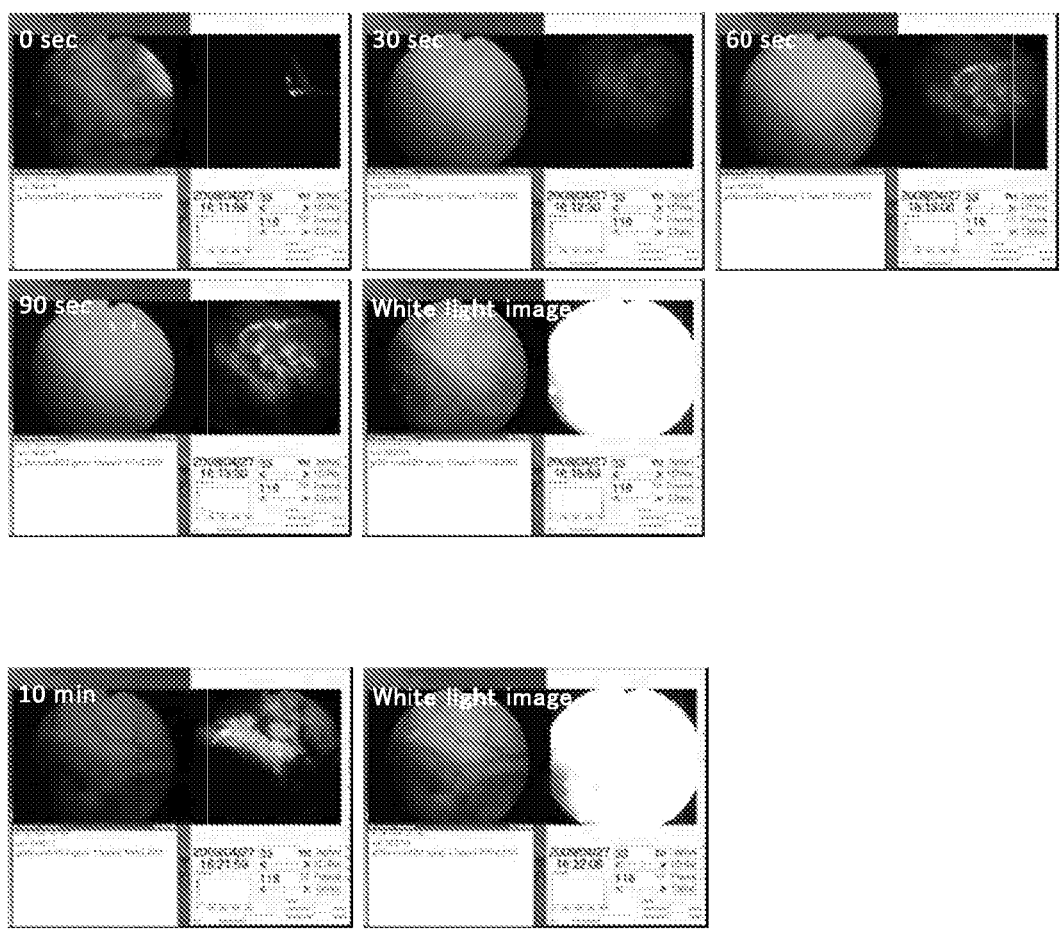
FIG. 4 This figure shows images obtained by live imaging using a fluorescence endoscope with Compound (2). In each of the results obtained immediately after spray (0 sec), and 30 seconds, 60 seconds, 90 seconds, and 10 minutes after the spray, a white light image is shown on the left side, and a fluorescence image is shown on the right side. The "white light image" is an image obtained in a usual endoscope mode, not a fluorescence mode, for comparison.

A small hole was formed in the abdominal part of the peritoneal dissemination model mouse under isoflurane anesthesia, a fluorescence endoscope was inserted into the abdominal cavity through the hole, and 300 μL of a solution of Compound (2) (γGlu-RhoHM) in PBS (50 μM) was sprayed in a misty state from the tip of the endoscope. Then, an excitation light of 450 to 480 nm was irradiated, and fluorescence of 516 to 556 nm was observed over time to obtain fluorescence endoscope movies and images. The results are shown in FIG. 4. In each of the results obtained immediately after the spray (0 sec), and 30 seconds, 60 seconds, 90 seconds, and 10 minutes after the spray, a white light image is shown on the left side, and a fluorescence image is shown on the right side. The "white light image" is an image obtained in a usual endoscope mode, not a fluorescence mode for comparison. It can be confirmed that the cancerous tissue images became clearer in the fluorescence images from immediately after the spray to 90 second thereafter. Further, even after 10 minutes, the cancerous tissues were clearly imaged (similarly, the "white light image" is an image obtained in a usual endoscope mode for comparison, not in a fluorescence mode). As a result, it was observed that a cancerous part was made to specifically emit fluorescence within several minutes by using the agent for diagnosing cancer of the present invention.

The invention claimed is:

1. A method for identifying the presence of gastric, lung, breast, colon, liver, gall bladder, pancreas, ovarian, peritoneal dissemination or lymph node cancer cells or tissue, comprising:

applying a compound of formula (I), or a salt thereof, to gastric, lung, breast, colon, liver, gall bladder, pancreas, ovarian, peritoneal dissemination or lymph node cells or tissue of a living body,

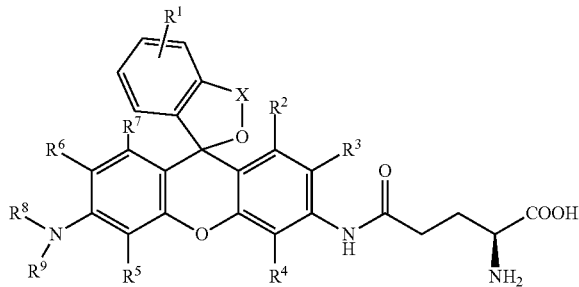

wherein $R^1$ represents a hydrogen atom, or the same or different one to four substituents binding to the benzene ring wherein the substituent is selected from the group consisting of an alkyl group, an alkoxyl group, a halogen atom, an amino group, a substituted silyl group, and an acyl group; $R^2$, $R^3$, $R^4$, $R^5$, $R^6$, and $R^7$ independently represent a hydrogen atom, a $C_1$-$C_4$ alkyl group, or a halogen atom; $R^8$ and $R^9$ independently represent a hydrogen atom, or a $C_1$-$C_4$ alkyl group; and X represents a $C_1$-$C_3$ alkylene group; and detecting fluorescence emitted by a compound of formula (II), which is generated from compound (I) in the presence of gastric, lung, breast, colon, liver, gall bladder, pancreas, ovarian, peritoneal dissemination or lymph node cancer cells or tissue,

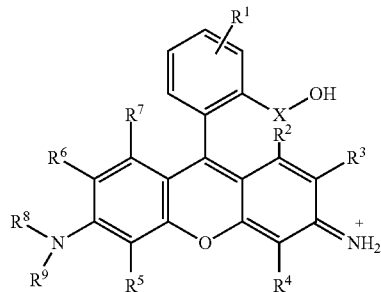

wherein $R^1$ represents a hydrogen atom, or the same or different one to four substituents binding to the benzene ring wherein the substituent is selected from the group consisting of an alkyl group, an alkoxyl group, a halogen atom, an amino group, a substituted silyl group, and an acyl group; $R^2$, $R^3$, $R^4$, $R^5$, $R^6$, and $R^7$ independently represent a hydrogen atom, a $C_1$-$C_4$ alkyl group, or a halogen atom; $R^8$ and $R^9$ independently represent a hydrogen atom, or a $C_1$-$C_4$ alkyl group; and X represents a $C_1$-$C_3$ alkylene group; and wherein the fluorescence emitted by a compound of formula (II) is indicative of the presence of the gastric, lung, breast, colon, liver, gall bladder, pancreas, ovarian, peritoneal dissemination or lymph node cancer cells or tissue, which fluorescence is observable in tumors equal to or greater than 0.1 mm immediately after application.

2. The method for identifying the presence of gastric, lung, breast, colon, liver, gall bladder, pancreas, ovarian, peritoneal dissemination or lymph node cancer cells or tissue according to claim 1, wherein each of $R^1$, $R^2$, $R^3$, $R^4$, $R^5$, $R^6$, $R^7$, $R^8$, and $R^9$ is a hydrogen atom, and X is a methylene group.

3. A method for treating gastric, lung, breast, colon, liver, gall bladder, pancreas, ovarian, peritoneal dissemination or lymph node cancer comprising:

performing the method for identifying the presence of the gastric, lung, breast, colon, liver, gall bladder, pancreas, ovarian, peritoneal dissemination or lymph node cancer cells or tissue according to claim 1; and performing diagnostic or therapeutic resection of the gastric, lung, breast, colon, liver, gall bladder, pancreas, ovarian, peritoneal dissemination or lymph node cancer cells or tissue.

4. The method according to claim 3, wherein the cancerous tissue is surgically resected in an open surgery, an endoscopic surgery, or endoscopy.

5. The method for identifying the presence of gastric, lung, breast, colon, liver, gall bladder, pancreas, ovarian, peritoneal dissemination or lymph node cancer cells or tissue according to claim 1, wherein the method is performed during surgery.

6. The method for identifying the presence of gastric, lung, breast, colon, liver, gall bladder, pancreas, ovarian, peritoneal dissemination or lymph node cancer cells or tissue according to claim 1, wherein the method is performed to identify a region to be excised.

7. The method for identifying the presence of gastric, lung, breast, colon, liver, gall bladder, pancreas, ovarian, peritoneal dissemination or lymph node cancer cells or tissue according to claim 1, wherein the applying comprises spraying.

8. The method for identifying the presence of gastric, lung, breast, colon, liver, gall bladder, pancreas, ovarian, peritoneal dissemination or lymph node cancer cells or tissue according to claim 2, wherein the applying comprises spraying.

9. The method according to claim 3, wherein the applying comprises spraying.

10. The method according to claim 4, wherein the applying comprises spraying.

11. The method for identifying the presence of gastric, lung, breast, colon, liver, gall bladder, pancreas, ovarian, peritoneal dissemination or lymph node cancer cells or tissue according to claim 5, wherein the applying comprises spraying.

12. The method for identifying the presence of gastric, lung, breast, colon, liver, gall bladder, pancreas, ovarian, peritoneal dissemination or lymph node cancer cells or tissue according to claim 6, wherein the applying comprises spraying.

13. The method for identifying the presence of gastric, lung, breast, colon, liver, gall bladder, pancreas, ovarian, peritoneal dissemination or lymph node cancer cells or tissue according to claim 7, wherein the fluorescence is observable after application for a period of time greater than 10 minutes.

14. The method for identifying the presence of gastric, lung, breast, colon, liver, gall bladder, pancreas, ovarian, peritoneal dissemination or lymph node cancer cells or tissue according to claim 8, wherein the fluorescence is observable after application for a period of time greater than 10 minutes.

15. The method according to claim 9, wherein the fluorescence is observable after application for a period of time greater than 10 minutes.

16. The method according to claim 10, wherein the fluorescence is observable after application for a period of time greater than 10 minutes.

17. The method for identifying the presence of gastric, lung, breast, colon, liver, gall bladder, pancreas, ovarian, peritoneal dissemination or lymph node cancer cells or tissue according to claim 11, wherein the fluorescence is observable after application for a period of time greater than 10 minutes.

18. The method for identifying the presence of gastric, lung, breast, colon, liver, gall bladder, pancreas, ovarian, peritoneal dissemination or lymph node cancer cells or tissue according to claim 12, wherein the fluorescence is observable after application for a period of time greater than 10 minutes.

19. The method for identifying the presence of gastric, lung, breast, colon, liver, gall bladder, pancreas, ovarian, peritoneal dissemination or lymph node cancer cells or tissue according to claim 2, wherein the fluorescence is observable after application for a period of time greater than 10 minutes.

20. The method for identifying the presence of gastric, lung, breast, colon, liver, gall bladder, pancreas, ovarian, peritoneal dissemination or lymph node cancer cells or tissue according to claim 5, wherein the fluorescence is observable after application for a period of time greater than 10 minutes.

* * * * *